US008088367B2

(12) United States Patent
Hillbur et al.

(10) Patent No.: US 8,088,367 B2
(45) Date of Patent: Jan. 3, 2012

(54) GALL MIDGE PHEROMONE MIXTURE

(75) Inventors: Ylva Birgitta Hillbur, Södra Sandby (SE); Martin Nils Gustav Andersson, Sjobo (SE)

(73) Assignee: PheroNet AB, Alnar (SE)

( * ) Notice: Subject to any disclaimer, the term of this patent is extended or adjusted under 35 U.S.C. 154(b) by 0 days.

(21) Appl. No.: 12/469,061

(22) Filed: May 20, 2009

(65) Prior Publication Data

US 2009/0274645 A1 Nov. 5, 2009

Related U.S. Application Data

(63) Continuation of application No. PCT/SE2007/050787, filed on Oct. 26, 2007.

(30) Foreign Application Priority Data

Nov. 20, 2006 (SE) ...................................... 0602496

(51) Int. Cl.

*A01N 31/02* (2006.01)
*A01N 37/06* (2006.01)
*A01P 19/00* (2006.01)

(52) U.S. Cl. ........................... 424/84; 514/549; 514/739

(58) Field of Classification Search ........................ None
See application file for complete search history.

(56) References Cited

FOREIGN PATENT DOCUMENTS

| WO | 9209199 | 6/1992 |
|---|---|---|
| WO | 9959408 | 11/1999 |

OTHER PUBLICATIONS

Andersson et al., Identification of Sex Pheromone Components of the Hessian Fly, Mayetiola destructor, J. Chem. Ecol. (2009), vol. 35, pp. 81-95.*

Foster et al., "Identification of the Sex Pheromone of the Hessian Fly, Mayetiola destructor (Say)"; 1991 Naturwissenschaften, vol. 78, pp. 130-131.

* cited by examiner

*Primary Examiner* — Johann Richter
*Assistant Examiner* — Frank Choi
(74) *Attorney, Agent, or Firm* — Gesmer Updegrove LLP

(57) ABSTRACT

The present invention relates to a pheromone composition for attracting male Hessian fly, *Mayetiola destructor* (Say), for monitoring and/or combating purpose, said composition consisting of (2S,10E)-I-O-tridecen-2-yl acetate (2S-E10-13:OAc), (2S)-tridecan-2-yl acetate (2S-13:OAc), (2S,10E)-10-tridecen-2-ol (2S-E10-13OH), and optionally (2S,8E,10E)-8,10-tridecadien-2-yl acetate (2S-E8-E10-13:OAc) and/or (2S,8Z,10E)-8,10-tridecadien-2-yl acetate (2S-Z8-E10-13:OAz), as well as a method for attracting said Hessian fly using such a composition.

5 Claims, 10 Drawing Sheets

A

B

GALL MIDGE PHEROMONE MIXTURE

TECHNICAL FIELD

The present invention relates to a mixture of sex pheromone active compounds to be used in attracting gall midges of the specie Hessian fly, *Mayetiola destructor* (Say), as well as a method for attracting such midges.

BACKGROUND OF THE INVENTION

Gall midges belong to the family Cecidomyiidae within the order Diptera. A gall midge life cycle consists of four separate stages: egg, larva, pupa and adult. The adult stage normally lasts only for a few days and during this period most gall midges do not feed. Adults are small, delicate flies measuring only a few millimeters in length. Gall midges exist all over the world and approximately 4,500 species are known, but probably many more exist. The Cecidomyiidae is a highly diverse family, including species that feed on plants, animals and fungi. Many of the plant-feeding gall midges are considered major agricultural pests.

The Hessian fly, *Mayetiola destructor* (Say) is one of the most destructive pests on wheat (*Triticum* spp) in the United States and North Africa, but it is also considered a pest in many European countries. Wheat is the most widely cultivated crop in the world, providing 20 percent of the calories consumed, and the Hessian fly is present in most of the major wheat growing areas. It is believed that the fly originated in Southwest Asia where wheat also originated. Since then, it has spread and its distribution today is almost global, ranging from North America in the west, throughout Europe and all the way to Siberia in the east. It can also be found as far south as Morocco, Cyprus and Iraq. On the southern hemisphere it is found on New Zealand. In North America it was probably introduced by Hessian soldiers during the war of Revolution or Independence in the 1700s. Therefore, the name Hessian fly was given to it 1778, although the first scientific description was not provided until 1817 by Thomas Say.

Although wheat is the preferred host, other grasses in the tribe Triticeae such as rye (*Secale cerale* L), barley (*Hordeum vulgare* L) and wild grasses, can also be used as hosts. Rye is the second most preferred host. In contrast, oat (*Avena sativa* L, tribe Aveneae) does not support development of Hessian fly larvae.

Life Cycle

Adult female Hessian flies emerge with a full complement of mature eggs Within a few minutes after emergence, females position themselves in a calling posture with their ovipositors extended and release a sexual pheromone to attract males When males sense the pheromone, they fly upwind towards the female Once a female is located, mating occurs quickly No male courtship behaviour occurs and females are almost always receptive on the first contact with a male Males mate several times if opportunity is given In contrast, females mate only once When mating is initiated, the female retracts her ovipositor and after mating, she sits inactive with her ovipositor retracted until oviposition begins 1 5-5 hrs later If females are not mated on their first day, they stop calling at about 113O h On day two they resume calling at about 0100 h and stop at about 1200 h with a peak between 0600-0800 h In virgins, this cyclic calling pattern is repeated at day three and four and continues until death, although virgins may start to lay unfertilized eggs at day three or four Mated females carry 50-400 eggs and oviposit on wheat leaves or some other possible host Normally, individual females produce unisexual progenies (all-male or all-female) The sex that is produced depends on the maternal genotype and is dependent on maintenance or elimination of the paternally derived sex chromosomes, which result in female and male progeny, respectively However, sometimes both sexes are produced, but then one sex often predominates Hessian fly eggs hatch after 3-5 days (FIG. 1) Soon after hatching on a leaf, the first instar larva migrates down the plant between the leaf sheets until it reaches the base of the plant where it establishes a feeding site, starts to feed and moults This is the only movement the larva does and it is thus restricted to the plant its mother chooses The second instar continues to feed and grow until it enters the third stage The duration of the larval feeding period ranges from 9-17 days The third non-feeding, immobile stage develops inside the second instar's skin, which is retained and scierotized to form a pupaπum, the so called "flaxseed" The pupa then develops, still inside the skin of the second larval instar The flaxseed stage normally lasts for about 12 days, but this varies depending on environmental conditions The adults emerge from the flaxseeds to complete the life cycle Adult males live for 1-2 days and virgin females for 3-4 days Mated females do not live as long as virgins and generally have less than a day to lay their eggs after mating One lifecycle can be completed in 20 days when conditions are optimal, but may also take up to 42 months if the third larval instar diapauses Generally, all stages develop faster in warm and moist conditions, whereas dry and cool as well as dry and hot weather will increase the generation time The number of generations per year ranges from one to six During the flaxseed stage, prevailing climatic conditions (i e temperature and relative humidity) determine if the larvae go through direct development, aestivation (oversummering) or diapause (overwintering). Since the climate determines the extent of aestivation and diapause, the number of generations per year is also dependent on the local climate. The number of generations and patterns of aestivation and diapause vary with latitude throughout North America.

Hessian Fly Damage and Deployed Control Methods

Damage from Hessian fly infestations can be quite extensive. When the larva has reached its feeding site it secretes a salivary substance that elicits release of plant nutrients. An attack results in differentiation of nutritive tissue around the feeding site and the larva is provided with a diet rich in amino acids and sugars. Hessian fly larval feeding does not result in macroscopic gall formations, instead the galls produced are referred to as simple galls. Plant cells below the attacking larva are inhibited from further growth, but are kept alive and are under constant stress from the larva. Larval feeding results in stunted growth. The stalks become weak and may break and if a seedling is attacked it normally dies. Moreover, attack on older plants result in fewer and/or smaller seeds, or seeds of low quality. Hessian fly infestations normally result in yield losses of economic importance, especially when infestation levels are high. In Morocco, an estimate of 32% of the wheat yield have been lost due to fly infestations and the outbreak 1988-1989 caused a $20 million loss in Georgia, USA. Clearly, Hessian fly populations must be controlled, but no control method used today is efficient enough.

Two main control methods are commonly used in the USA: (i) delayed planting and (ii) resistant wheat varieties. To some extent insecticides are used as well. These methods all have some disadvantages. The usage of delayed planting or "fly-free" planting dates to avoid fall infestations have been used since 1799. Hessian flies emerge during fall from old wheat stubble, volunteer wheat or from other grass hosts. By planting after fly activity has ceased, female flies are forced to lay their eggs on other hosts than wheat. This method has successfully reduced fall infestations in the northern USA where only one fall generation occurs and the fly diapauses during winter. However, by delaying planting in the southern parts of USA where additional fall and winter generations exist, fall damage is normally reduced, but the risk of spring damage is increased. Moreover, recommended planting dates are based on typical years and may not be effective if emergence is late. An additional problem with this method is that the later planting date reduces yield since the growth season is shortened and the risk of cold injury increases.

While delayed planting is of limited use and normally only affects fall infestations, using wheat cultivars resistant to Hessian fly attack provide full season control and has been the most effective and economic control method So far, 29 different resistance (R) genes have been found By incorporating one of these into the cultivated wheat variety, Hessian fly larvae do not establish or grow and typically die within two to five days after arrival at the feeding site The problem is that the R genes impose a heavy selection pressure on the flies that evolve to become more virulent and eventually overcome the resistance In Indiana 1955, a cultivar carrying an R gene was deployed and provided efficient resistance However, after six years the flies had evolved counter-resistance Then a cultivar carrying a second R gene was released 1964, with counter-resistance appearing within eight years 1971, a third gene was released and counter-resistance had evolved within 10 years Due to the deployment of different resistant wheat cultivars, 16 Hessian fly biotypes in the USA have evolved that only differ in their ability to infest and survive on specific resistant wheat varieties As a consequence, new R genes must constantly be identified and incorporated into wheat cultivars This is very costly and time consuming, and it is often difficult to combine resistance with satisfactory straw strength, earliness and grain quality As a result, resistant wheat normally gives lower yield compared to susceptible cultivars when Hessian fly damage is absent Moreover, R genes are thought to be of limited numbers and should not be wasted Although not widely practiced, spraying insecticides at planting have the potential to reduce fall, winter and spring damage without subsequent yield losses But, since early infestations of Hessian fly are extremely difficult to detect, insecticides must be used as a preventative strategy Besides the potential negative effects on the environment and farmers' health, spraying insecticides also kills the flies' parasitoid enemies In addition, insecticide usage when it is not needed is an unnecessary cost for the farmer.

Sexual Pheromones in Hessian Fly Control

Early infestations of Hessian fly are difficult to detect for several reasons First, all life stages are very small, adults have a highly synchronized eclosion and flight activity, and may be present in the crop for a very short period of time due to their short lifespan Second, the larvae feed inside the stem, the damage they produce is subtle and the young plants often give a false impression of well-being due to their erectness and darkish-green colouration As a consequence, flies are normally detected after they have become a serious problem Third, outbreaks are typically sporadic and hence difficult to predict The aestivation and diapause habits of the fly make them survive unfavourable environmental conditions for long periods When conditions return to favourable, aestivation or diapause is terminated, and suddenly flies are present in the crop again Female sex pheromones for control of Hessian fly populations are a realistic solution to the control problems, without direct negative effects on the environment. By using traps baited with synthetic versions of the pheromone, useful information about the Hessian fly population can be obtained. The traps can be used to detect the presence of flies as well as the timing of their flight activity in the field. Moreover, traps can be used to estimate population levels to decide if other control methods (e.g. resistant wheat varieties or insecticides) are necessary and/or economical. If a pheromone based monitoring system was used, the farmer would have the ability to avoid unnecessary yield losses and environmental pollution. However, the sex pheromone must be chemically identified before it can be used in a monitoring system. Once the pheromone is identified, pheromone based monitoring is a method that can be used by the individual farmer. It does not require entomological skills since the pheromone is species specific. In addition, pheromones can be used in an attract-and-annihilate method, where males are attracted to a site where they are removed from the environment (i.e. killed). Mating disruption is another method that can be used for control of pest populations. In this method, synthetic pheromones are released at a high enough amount to disrupt mate finding. It is however unclear if the attract-and-annihilate method and mating disruption can be used for Hessian fly control. Both methods are used to reduce pest populations and they are most efficient at low population densities. Therefore, they have greater utility in preventing outbreaks (which may not be economical for Hessian fly control), rather than reducing the population during an outbreak. An additional problem with the use of these methods for Hessian fly control is the practice of crop rotation. The attract-and-annihilate method or mating disruption must be carried out in the emergence field, and if crops are rotated, flies might not emerge in a wheat field. Therefore, the deployment of these methods might be difficult, especially if the farmers are unwilling to control an insect that is pest of a crop that they are not currently growing.

Pheromone based monitoring systems have been developed and commercialized for at least two Cecidomyiids: the pea midge, *Contaŋnia pisi* (Hillbur et al 2000) and the swede midge *C. nasturtii* (Hillbur et al 2005), although opportunities exist for the orange wheat blossom midge, *Sitodiplosis mosellana*, Douglas-fir cone gall midge, *C. oregonensis*, red cedar cone midge, *Mayetiola thujae*, and the *aphidophagous gall* midge, *Aphidoletes aphidimyza.*

The Hessian fly pheromone To date, 13 cecidomyiid species are known to use sex pheromones, however, pheromone compounds have been identified only for seven of those (Table 1). The identified cecidomyiid pheromone compounds show a striking similarity in their chemical structure.

Most compounds are 13-carbon chains with a functional group (often an acetate group) in C-2 position, although some species have shorter or longer carbon chains.

TABLE 1

Species in *Cecidomyiidae* known to have sexual pheromones (modified from Hillbur 2001).

| Species | Field trapping | Laboratory bioassays | Compound identification |
|---|---|---|---|
| Hessian fly *Mayetiola* destructor | Cartwright (1922) | McKay and Hatchett (1984) Harris and Foster (1991) | Foster et al (1991b) |
| Red cedar cone midge *Mayetiola thujae* | Gries et al (2005) | | Gries et al (2005) |
| *Brassica* pod midge *Dasineura brassicae* | Williams (1990) | Williams and Martin (1986) | |
| Blackcurrant leaf midge *Dasineura tetensi* | Garthwaite and Wall (1986) | | |

TABLE 1-continued

Species in *Cecidomyiidae* known to have sexual pheromones (modified from Hillbur 2001).

| Species | Field trapping | Laboratory bioassays | Compound identifi-cation |
|---|---|---|---|
| Apple leaf curling midge *Dasineura mali* | Harris et al (1996) | Harris et al (1996) | |
| Douglas-fir cone gall midge *Contarinia oregonensis* | Miller and Borden (1981) Gries et al (2002) | Miller and Borden (1984) | Gries et al (2002) |
| Pea midge *Contarinia pisi* | Wall et al (1985) Hillbur et al (2000) | Hillbur and Löfqvist (1996) Hillbur et al (2000) | Hillbur et al (1999) |
| Sorghum midge *Contarinia sorghicola* | Sharma and Vidyasagar (1992) | | |
| Swede midge *Contarinia nasturtii* | Hillbur et al (2005) | Hillbur et al (2005) | Hillbur et al (2005) |
| Orange wheat blossom midge *Sitodiplosis mosellana* | Pivnick (1993) Gries et al (2000) | Pivnick (1993) | Gries et al (2000) |
| Pine gall midge *Thecodiplosis japonensis* | | Lee and Lee (1985) | |
| Rice midge *Orseolia oryzae* | Sain and Kalode (1985) | | |
| Aphidophagous gall midge *Aphidoletes aphidimyza* | Choi et al (2004) | Choi et al (2004) | Choi et al (2004) |

The first observation that indicated that Hessian fly females release a long-range sex pheromone was done by Cartwright (1922) He placed cages containing females in the field and observed that males flew upwind towards the females at distances within 15 feet Decades later it was shown, in a Y-tube olfactometer bioassay, that males were attracted to females with extended ovipositors as well as to hexane washes of female ovipositors. They also found that female sexual attractiveness and mating activity seemed to be regulated by extension and retraction of the ovipositor and that female attractiveness followed a diurnal rhythm. Their results suggested that the ovipositor is the pheromone release site. Later it was found that the ovipositor contains gland tissue, indicating that it is also the site of pheromone production.

The first compound in the Hessian fly pheromone to be identified was (2S,10£)-10-tridecen-2-yl acetate (2S-E10-13:OAc). Virgin females were shown to contain a relatively large amount (ca 2 ng) of this compound shortly after emergence and then declining amounts for at least the next 8 hours of the photophase. However, in the early mornings of the second and third days, the amount of pheromone in virgins was high again and with the same patterns of declining amounts during subsequent hours. In contrast, mated females do not continue to produce pheromone.

The attractiveness of 2S-E10-13:OAc to male Hessian flies was studied in a wind tunnel by Harris and Foster (1991). Only 56% of the males contacted the odour source when 2S-E10-13:OAc was used as stimulus, whereas 87% contacted the source when female ovipositor extract was used. This result indicated that the sex pheromone consists of at least one additional compound. Thus the male response was also measured to binary blends of 2S-E10-13:OAc and racemic mixtures of three other chemicals, found in female extract: (10Z)-10-tridecen-2-yl acetate (Z10-13OAc)$_1$ (10E)-10-tridecen-2-ol (E10-13OH) and tridecan-2-yl acetate (13:OAc).

However, none of these blends attracted more males than did 2S-E10-13:OAc alone. In a field study, the main compound (2S-E10-13:OAc) did not catch any male Hessian flies, but instead caught another so far unidentified cecidomyiid. Additional results from a semi-field test (Hillbur et al unpublished) have shown that a tertiary blend of 2S-E10-13:OAc, 2S-E10-13OH and 2S-13:OAc caught significantly more males than the main compound alone and blank traps. Furthermore, coupled gas chromatographic-electroantennographic detection (GC-EAD$_1$ Arm et al 1975) has shown that these three compounds elicit antennal responses in male Hessian flies (Hillbur et al unpublished).

However, the three-component blend has not been tested behaviourally under controlled laboratory conditions and its attractiveness has not been compared to female pheromone extract. GC-EAD analyses of female extract have also revealed additional, so far unidentified compounds that elicit antennal responses. Chemical analyses of gland extract have shown that one of the unidentified compounds is a double-unsaturated $C_{13}$ acetate. An unsaturated $C_{15}$ acetate has also been found in gland extract, but it is not known if it corresponds to one of the antennally active compounds. The chemical identification of these compounds is difficult since they exist in minute amounts in female extract. Because of this, the stereochemistry and the position of the double bonds are unclear, but four candidate compounds have been proposed (Hillbur et al unpublished).

SUMMARY OF THE PRESENT INVENTION

The present invention relates to the identification of the Hessian fly sex pheromones by testing the male antennal response to four tentative pheromone compounds. For verification of previous results, the three compounds that have previously been shown to elicit antennal responses in GC-EAD analyses were included as well. In the process of identifying pheromone compounds, it is also essential to investigate the behavioural effects of the compounds under study. Therefore, behavioural tests using a Y-tube olfactometer where the attractiveness of different synthetic pheromone blends was compared with the attractiveness of female ovipositor extract were studied as well to support the inventive concept.

BRIEF DESCRIPTION OF THE DRAWINGS

These and other objects, features and advantages of the present invention will become apparent in light of the following detailed description of preferred embodiments thereof, as illustrated in the accompanying drawings.

DETAILED DESCRIPTION OF THE PRESENT INVENTION

Figure 1:
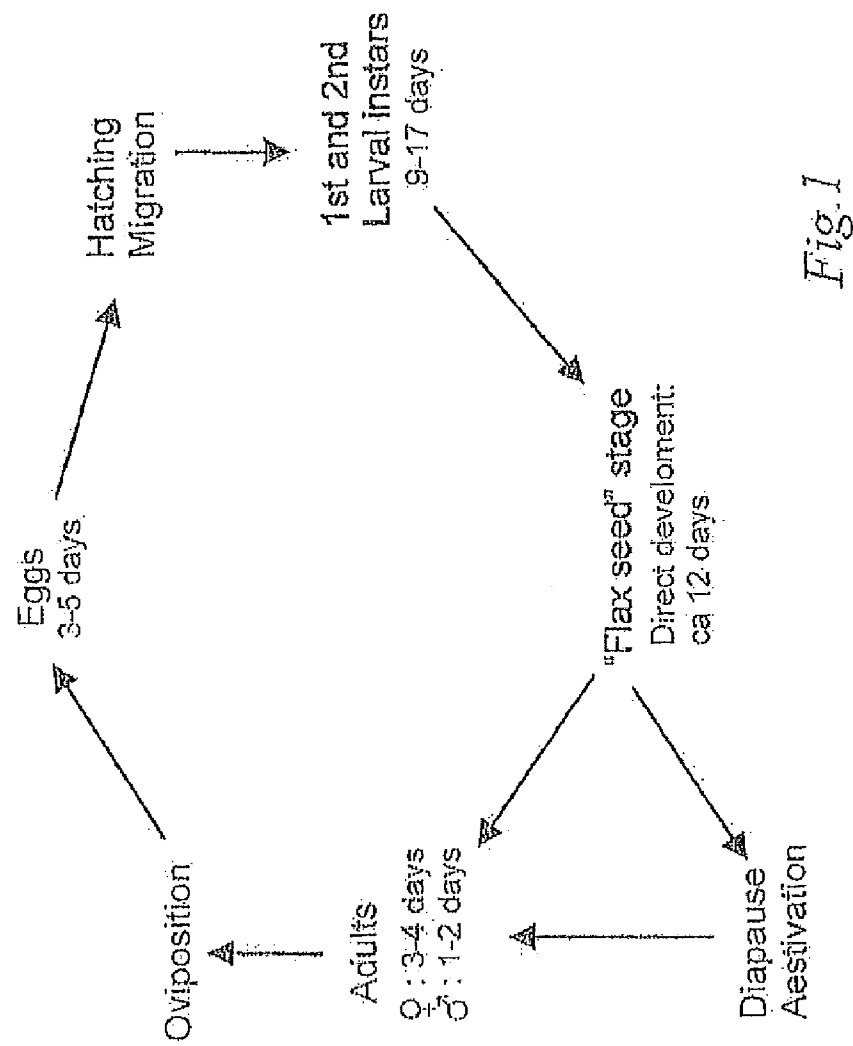
FIG. 1. is a Hessian fly life cycle.

In particular the present invention relates to a mixture of pheromone active compounds, which mixture elicits an attractivity effect being close to the one of the female Hessian fly. The invention in one aspect also relates to a method for inhibiting the mating of Heesian fly, as well as monitoring the presence of Hessian fly.

In particular the invention relates to a pheromone composition for attracting male Hessian fly, *Mayetiola destructor* (Say), for monitoring and/or combating purpose, said composition consisting of (2S)-tridecan-2-yl acetate (2S-13:OAc), (2S,10E)-10-tridecen-2-yl acetate (2S— E10-13:OAc), and (2S, 10E)-10-tridecen-2-ol (2S-E10-13:OH).

In a preferred embodiment thereof it further consists of (2S,8£,10E)-8,10-tridecadien-2-yl acetate (2S-E8-E10-13:Oac)

In a preferred embodiment thereof it further consists of (2S,8Z,10E)-8,10-tridecadien-2-yl acetate (2S-Z8-E10-13:OAc).

In a preferred embodiment thereof it consists of (2S,10£)-10-tridecen-2-yl acetate (2S-E10-13:OAc), (2S)-tridecan-2-yl acetate (2S-13:OAc), (2S$_1$10E)-1O-tridecen-2-ol (2S-E10-13OH)$_1$(2S,8E,10E)-8,10-tridecadien-2-yl acetate (2S-E8-E10-13:OAc) and (2S,8Z,10£)-8,10-tridecadien-2-yl acetate (2S-Z8-E10-13:OAc).

In a preferred embodiment thereof the ratio between (2S-E10-13:OAc), (2S-13:OAc), and (2S-E10-13OH) is 10:1:1.

In a preferred embodiment thereof the ratio between (2S-E10-13:OAc), (2S-13:OAc), (2S— E10-13:OH) and (2S-E8-E10-13:OAc) is 10:1:1:1.

In a preferred embodiment thereof the ratio between (2S-E10-13:OAc), (2S-13:OAc), (2S— E10-13:OH), (2S-E8-E10-13:OAc) and (2S-Z8-E10-13:OAc) is substantially 10:1:1:1:1.

A further aspect of the invention relates to a method for attracting male Hessian fly, *Mayetiola destructor* (Say), characterized in that a composition consisting of (2S,10£)-10-tridecen-2-yl acetate (2S-E10-13:OAc), (2S)-tridecan-2-yl acetate (2S-13:OAc), (2S,10E)-10-tridecen-2-ol (2S-E10-13OH), is dispersed in an attracting amount in an environment comprising said Hessian fly.

Insect Rearing

Infested wheat containing Hessian fly puparia was provided by Dr. Jeffrey J. Stuart (Purdue University, West Lafayette, Ind., USA) and Dr. Marion O. Harris (North Dakota State University, Fargo, N. Dak., USA). The plant material was put in Plexiglas cages (29×34×29 cm) that were placed in a climatic chamber (25° C., 70% RH and a 12:12 LD photoperiod; lights on 0900 h) for the adults to emerge. Typically, the adults emerged 7-14 days after the puparia were placed in the chamber. Mated females were transferred to larger cages (33×33×33 cm) where they were allowed to oviposit on wheat. The cages contained three pots (height: 12 cm; diameter: 15 cm), each with ca 100 wheat plants in the third leaf stage. The bottom of the cage was covered with a thin layer of moist soil. During 1-2 weeks, mated females were allowed to infest the wheat in one cage. After two weeks, a new cage with wheat was used for infestation. During the period of infestation, the cages were kept under the same conditions as described above. However, in order to promote larval development and thus increase the number of emerging adults, the cages were then transferred to another climatic chamber (21° C., 60% RH and 12:12 LD photoperiod; lights on 0900 h). Adults started to emerge after approximately 25 days, with an emergence peak after ca 30 days and thereafter declining emergence until it completely ceased ca 40 days after infestation. To avoid desiccation of developing flies, infested wheat in all cages were sprayed daily with a fine mist of water. Transfer of insects was done with an aspirator or a small glass tube.

Pheromone Extraction

Figure 2:
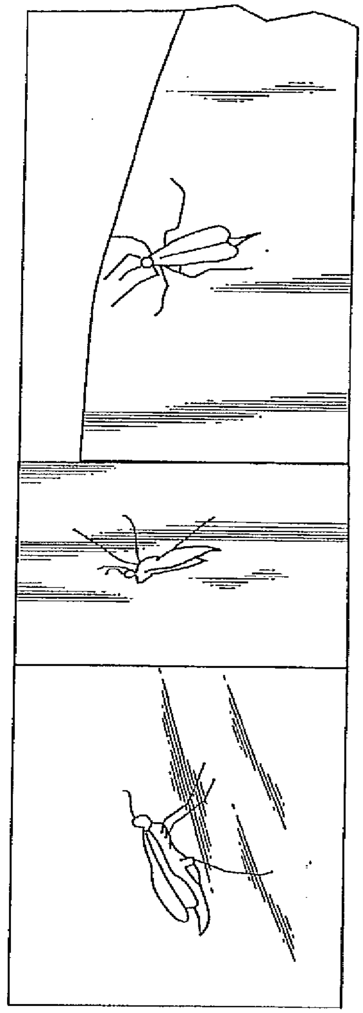
FIG. 2. illustrates a general representation of the Hessian flies.

Virgin females were easily distinguished from mated females since virgins sit in a calling posture with the ovipositor clearly extended (FIG. 2). Female Hessian flies have a dark color, i.e. a brown-black/red color. Gland extracts were prepared by excising the ovipositors of calling females. The ovipositors were collected in a vial kept in liquid nitrogen and then extracted for 1-1.5 min in redistilled hexane (LabScan AB). The extracts were then transferred into glass vials and kept in a freezer at −18° C. until use.

All extractions were made between 0900 h and 113O h.

GC-EAD Recordings

Figure 3:
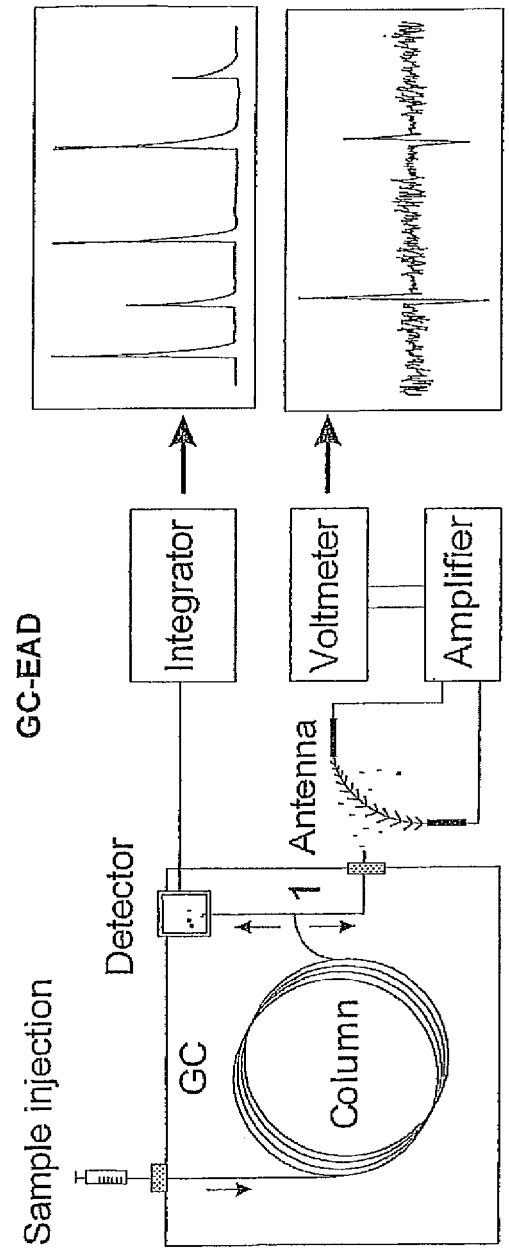
FIG. 3. An overview of a GC-EAD set-up Samples are injected on a GC with a split column (1) and an extra outlet in order to receive simultaneous recordings from the FID detector (upper right) and the antennal detector, EAD (lower right)

Coupled gas chromatographic-electroantennographic detection (GC-EAD$_1$ Am et al 1975) was used to analyse female gland extracts. GC-EAD is an efficient tool to determine which compounds in an extract that the male antennae can perceive, by use of the highly specific olfactory receptor neurons. In a GC-EAD set-up (FIG. 3), the effluent of the GC column is split between the flame ionisation detector (FID) of the GC and the antennal detector (EAD). The GC separates the compounds in the extract over time and the compounds are detected by the FID. Simultaneously, the eluting compounds also pass the male antennae via a constant charcoal-filtered and humidified air stream. The male antennae are connected to two electrodes and, if the antennae perceive a compound, neural signals are generated and these signals are recorded as an electroantennogram (EAG). Since the olfactory receptors on the antennae are highly specific, they will more or less exclusively respond to the pheromone compounds in the extract. In addition to pheromone extracts, GC-EAD can be used to analyse all sorts of compound blends, e.g. host volatile collections and synthetic pheromone compounds. Irrespective of what kind of substances that are analysed, simultaneous recordings from the FID and the EAD give information on which compounds in the blend that are interesting for chemical identification and/or behavioural testing.

In addition to gland extracts, GC-EAD was used to analyse seven synthetic compounds (Table 2). Three of these had previously been shown to elicit antennal responses by Hillbur et al (unpublished). The other four (tentative pheromone compounds) had never been tested for antennal responses with male Hessian flies before.

TABLE 2

Synthetic compounds tested for antennal responses.

| | |
|---|---|
| (2S)-tridecan-2-yl acetate | (2S-13:OAc) * |
| (2S,10E)-10-tridecen-2-yl acetate | (2S-E10-13:OAc) * |
| (2S,10E)-10-tridecen-2-ol | (2S-E10-13:OH) * |
| (2S,8z,10E)-8,10-tridecadien-2-yl acetate | (2S-Z8-E10-13:OAc) ** |
| (2S,8E,10E)-8,10-tridecadien-2-yl acetate | (2S-E8-E10-13:OAc) ** |
| (2S,10E)-10-pentadecen-2-yl acetate | (2S-E10-15:OAc) ** |
| (2S,12E)-12-pentadecen-2-yl acetate | (2S-E12-15:OAc) ** |

* = compounds known to elicit antennal responses

** = compounds previously not tested for antennal responses

Figure 4:
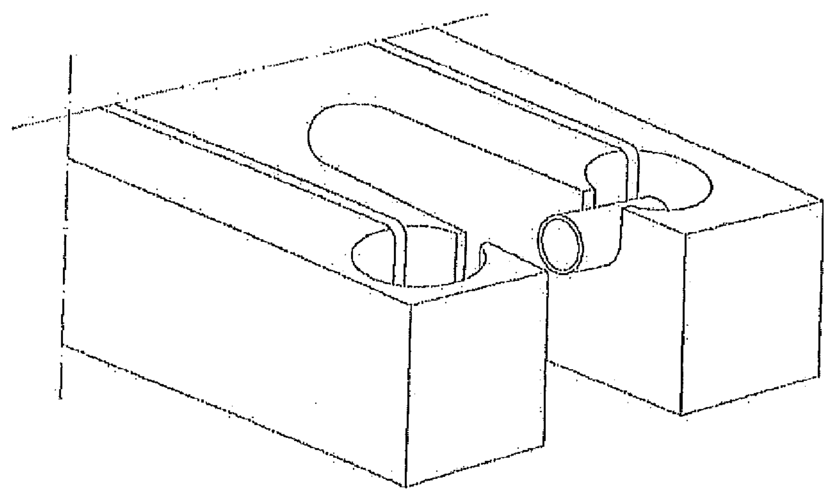
FIG. 4. The antennal holder used for GC-EAD recordings Males were placed in the holder by pressing the thorax into the slit of the left well The head and antennae protruded into the gap between the wells and the tips of the antennae were inserted into a small glass capillary positioned in the slit of the right well The wells and the capillary were then filled with saline to provide contact Figure from Hillbur (2001)

A Hewlett-Packard 6890 GC (Palo Alto, Calif., USA) with flame ionization detection and an Innowax column (30 m×0.25 mm ID, H-P) was used for the GC-EAD recordings. The column was programmed from 80° C./2 min to 220° C. at 10° C./min. Since male Hessian fly antennae are very sensitive to desiccation, whole male bodies instead of excised antennae were mounted in an antennal holder (JoAC, Lund, Sweden) (FIG. 4). The antennal holder is made of Plexiglas with two wells connected to an amplifier by gold wire electrodes and males were mounted in the antennal holder as described by Hillbur et al (2001). The antennae were exposed to a charcoal-filtered and humidified air stream at a rate of ca 0.3 m/s through a glass tube (8 mm diameter). The signals from the antennae were amplified (JoAC) before they were recorded and analysed with ElectroAntennoGraphy software (Syntech, Hilversum, The Netherlands).

Behavioural Experiments

Figure 5:
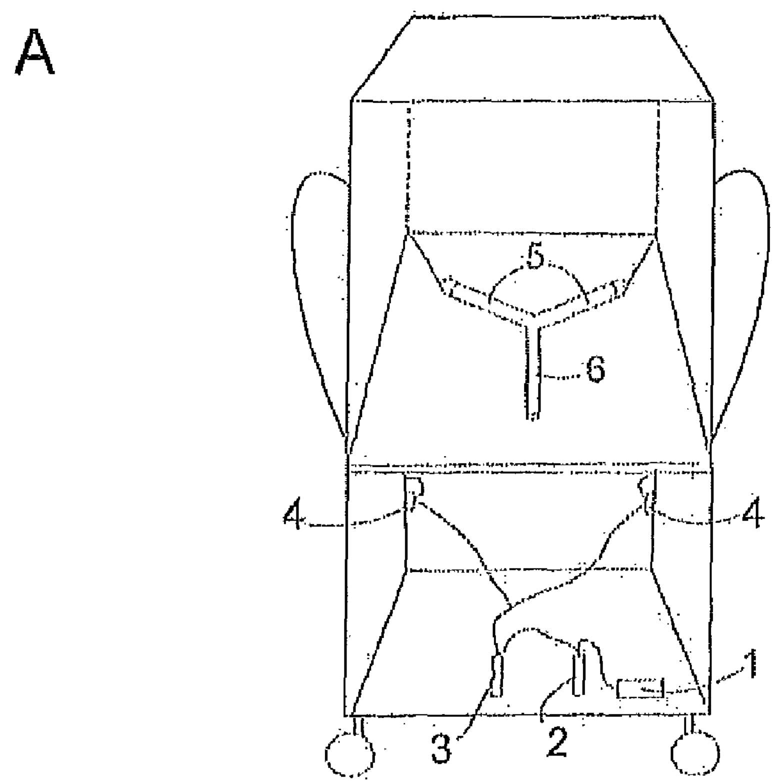
FIG. 5A. Mobile Y-tube olfactometer 1) pump, 2) charcoal filter, 3) air humidifier, 4) flow meters, 5) custom made glass tubes, 6) Y-tube b) Custom made glass tube holding filter paper with stimulus; and 5B. A teflon tuble in a custom made glass tube.
Figure 5:
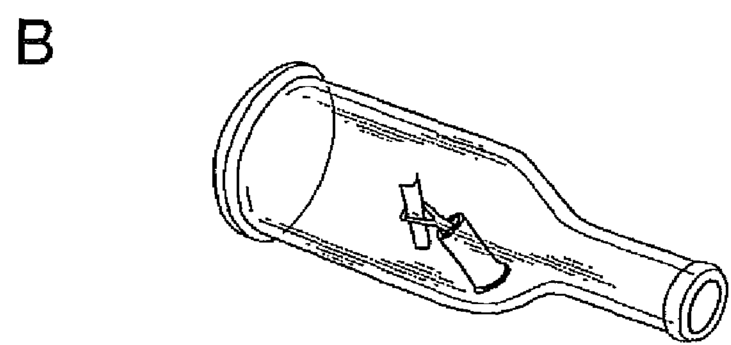

The attractiveness of different synthetic pheromone blends and female gland extracts were studied in a mobile glass Y-tube olfactometer, (FIG. 5A). The arms of the Y-tube were 14 cm long, the stem 12.5 cm and the inner diameter was 2.2 cm. Charcoal-filtered and humidified air was pumped (Micro pump NMP 30 KNDC, 12 V, KNF Neuberger, Germany) through Teflon tubes and entered each arm via a custom made 9.5 cm long glass tube, (Humi Glas, Sodra Sandby, Sweden) (FIG. 5B). The air inlet side of the tube had an outer diameter of 1.0 cm and was connected to the Teflon tube. The other side had a female ground and was connected to the male ground on each of the Y-tube arms. In the centre of the glass tube was a glass rod (ca 1 cm long; 0.5 cm diameter) containing a centred small hole. During experiments, the stimulus was applied on a small piece of filter paper (1.5×0.5 cm) attached to a ca 1.5 cm long steel wire. The steel wire was placed in the hole of the glass rod to position the stimulus in the centre of the tube. A fine mesh divided the glass tube from the Y-tube and prevented animals from flying into the Teflon tube system. To assure symmetric light intensities, the Y-tube was placed in a box (40×44×33 cm) that had its floor and lateral sides made of brown cardboard, while the roof and the front side was made of white fabric. The rear side was open. The stem of the Y-tube faced the open side and the arms faced the fabric-covered front. A 500 W halogen lamp (Massive, Belgium) was placed 60 cm from the front in order to increase the number of responding males.

Experiments were done between 0930 h and 113O h during the photophase in a climatic chamber with 25° C. and 70% RH. The air-flow through each arm of the Y-tube was 500 ml/min (BA-4AR, Kytóla, Muurame, Finland). During tests, males were taken from the rearing cages and immediately released into the stem of the Y-tube by means of small glass tubes (length: 5 cm; outer diameter: 2.1 cm). The tubes fitted precisely in the stem and were placed 5 cm into the stem. A fine mesh closed the rear end of the tube in order to prevent the males from escaping. All males were tested individually and were given 5 min to respond. A male was regarded as a responder if it had passed half the length (7 cm) of one side arm within 5 min. If a male passed half the length of one side arm, but then flew or walked back and into the other arm, the first arm was regarded as its choice. Non-responding males were not included in statistical analyses.

Six different two-choice bioassays were performed to evaluate differences in attractiveness of the main pheromone component (abbreviated: 7), 2S-E10-13:OAc, a three-component blend (abbreviated: 3) consisting of 2S-E10-13:OAc, 2S-E10-13OH and 2S-13:OAc, and two different four-component blends, both consisting of the compounds included in the three-component blend but with either 2S-E8-E10-13:OAc (abbreviated: 4E) or 2S-Z8-E10-13:OAc (abbreviated: 47) added. One of the synthetic blends was also compared with female pheromone gland extract of comparable concentration. In addition, a blank-blank (hexane only) treatment was performed to check for non-odour mediated directional preferences. The different blends had the following ratios between the main component and the other components: 100:10:10 (3) or 100:10:10:10 (4E and 47). 10 ng of the main component was applied to the filter papers during tests and a maximum of six consecutive males (or 10 min time limit) were tested before the filter papers were exchanged. All bioassays were run on at least three different days to reduce day effects. Potential non-odour mediated preferences were eliminated by switching sides of the two stimuli during a bioassay. All glass equipment was heated to 320° C. for 8 h before each day of testing. Data from the eight bioassays were analysed by chi-square tests.

GC-EAD Recordings

Figure 6A:
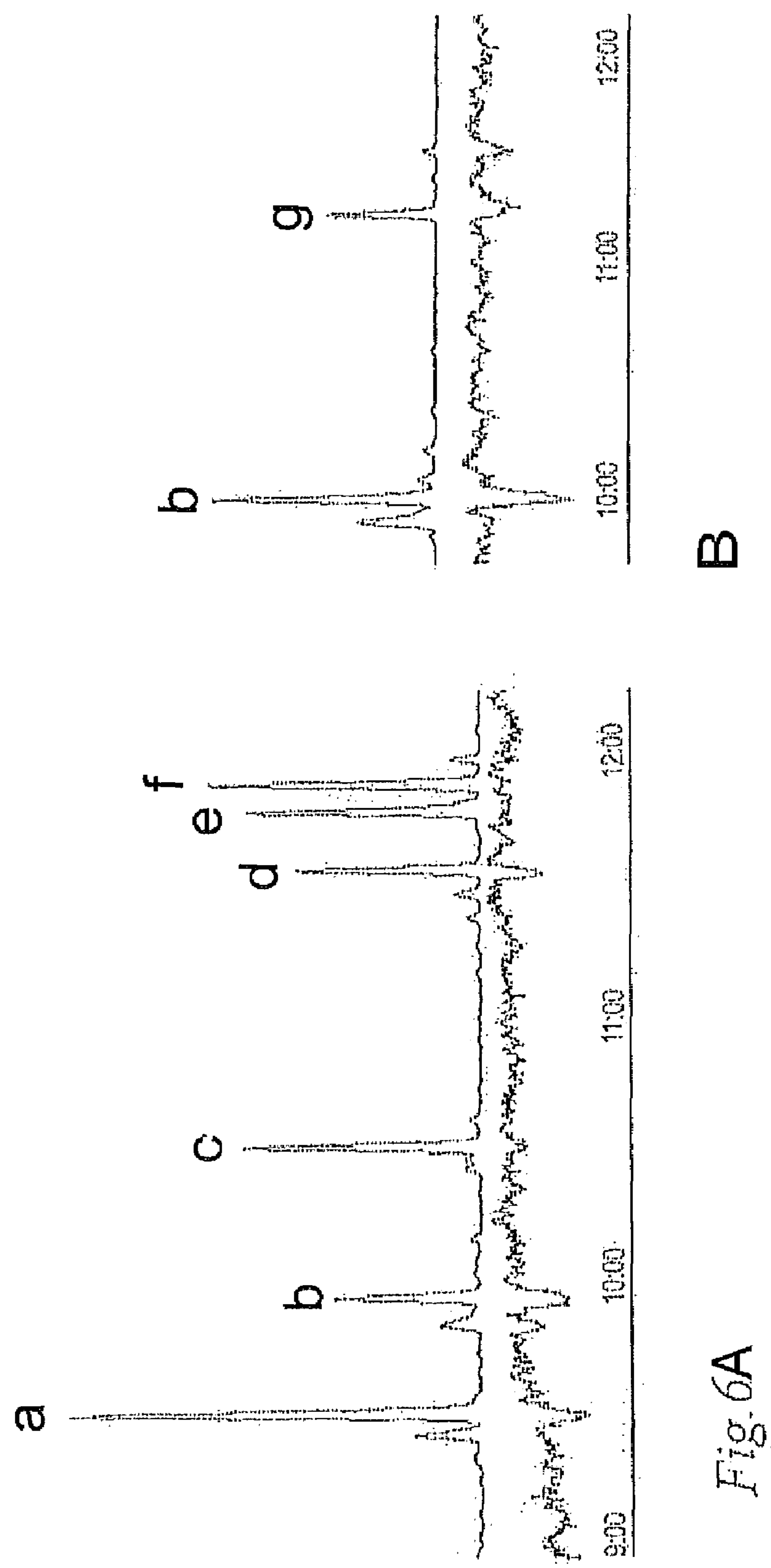
FIG. 6. GC-EAD recordings of male antennal responses to synthetic compounds a) Males responded to A 2S-13 OAC, B 2S-E10-13 OAc$_1$ C 2S-E10-13OH and D 2S-E8-E10-13 OAc No responses were recorded to E 2S-E10-15 OAc or F 2S-E12-15 OAc b) Males responded again to 2S-E10-13 OAc (B) and also to G 2S-Z8-E10-13 OAc Note A number of compounds, not indicated by capital letters are also present in the two synthetic blends It is likely that these compounds are isomers of the seven compounds tested and present in the blends because the isomeric purity of synthetic compounds was below 100% In a) a response was recorded just to the left of B This compound is 2S-Z10-13 OAc In b) a response was recorded to a compound just to the right of G, probably 2S-E8-E10-13 Oac.

Repeated GC-EAD recordings showed that five out of seven synthetic compounds elicited antennal responses in males. The compounds were: 2S-13:OAc, 2S-E10-13:OAc, 2S-E10-13:OH, 2S-E8-E10-13:OAc (FIG. 6A) and 2S-Z8-E10-13:OAc (FIG. 6B). Therefore, these compounds were used in different blends in the behavioural experiments. The retention time and mass spectrum of 2S-Z8-E10-13:OAc were similar to the double-unsaturated $C_{13}$ acetate found in gland extract (number 6 in FIG. 7). Moreover, the retention time of 2S-E8-E10-13:OAc seemed to correspond to the compound in gland extract (number 7 in FIG. 7) that was thought to be an unsaturated $C_{15}$ acetate. The unsaturated $C_{15}$ acetates (2S-E10-15:OAc and 2S-E12-15:OAc) did not elicit antennal responses (FIG. 6A) and the retention times did not fit with any of the antennally active compounds in gland extract (FIG.

Figure 7:
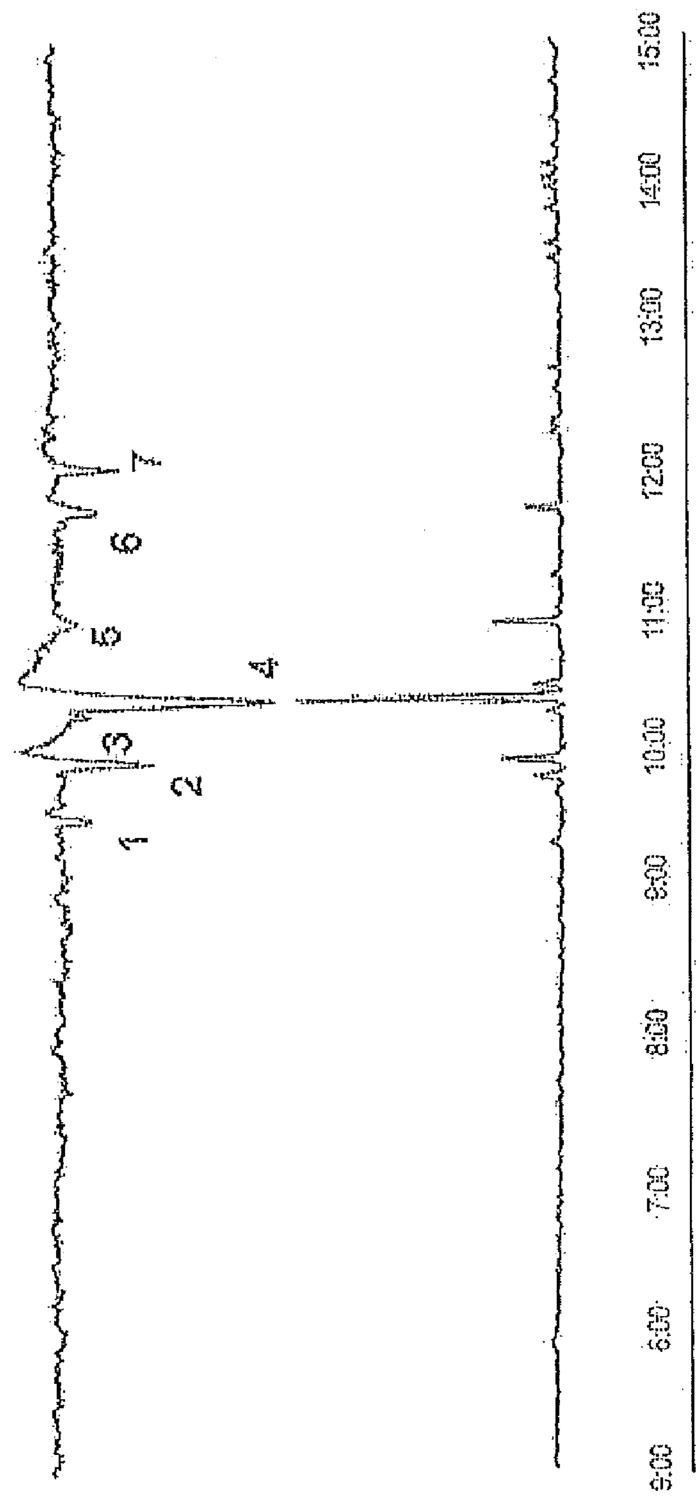
FIG. 7. GC-EAD response to female Hessian fly extract (20 female equivalents) showing antennal responses to seven compounds 1) unknown, 2) 2S-13 OAc, 3) 2S-Z10-13 OAc, 4) 2S-E10-13 OAc, 5) 2S-E10-13OH, 6) unknown, but possibly 2S-Z8-E10-13 OAc and 7) unknown, but possibly 2S-E8-E10-13 OAc or an unsaturated $C_{15}$ acetate (different from the ones tested (FIG. 6*a*)) Note this recording was done using a different column Hence, retention times are not comparable with the ones in FIG. 6.

7). These compounds were thus excluded from behavioural tests. Antennal responses to compounds in female gland extract are shown in FIG. 7.

Behavioural Experiments

The percentages of responding males were high in all bioassays, except in the blank-blank treatment (Table 3). Typically, when odours were present, males flew into one of the Y-tube arms within 20 seconds after release. In contrast, the response often occurred after 2-5 minutes in the blank-blank bioassay. In all bioassays, most responding males flew straight into one of the arms, although some males flew back and forth between the stem and the two arms before they finally made their choice. A small number of males did not fly, but instead walked into one of the arms.

TABLE 3

Sample sizes (N) and number as well as percentages of responding males for the eight bioassays.

Figure 8:
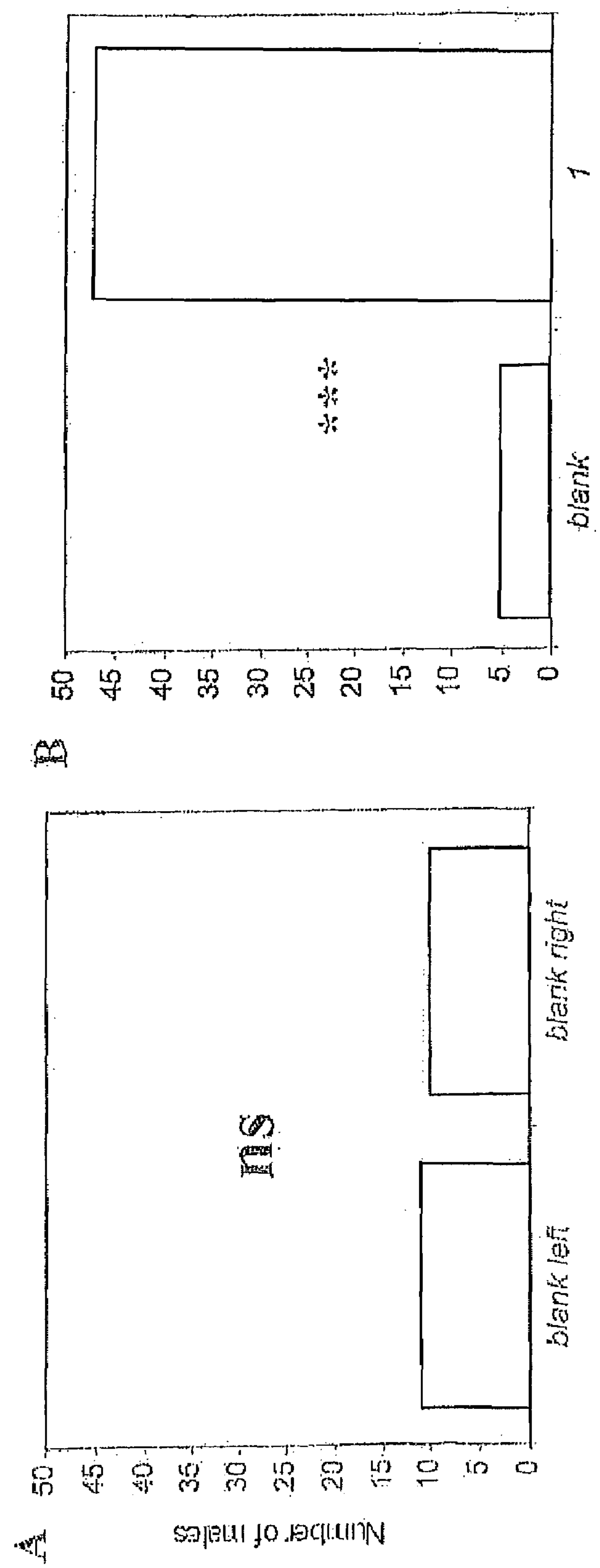
FIG. 8. Response of male Hessian flies in the two-choice bioassays Abbreviations 1 2S-E10-13 OAc (10 ng), 3 2S-E10-13 OAc, 2S-13 OAc and 2S-E10-13OH (10 1 1 ng), 4E 2S-E10-13 OAc, 2S-13 OAc, 2S-E10-13OH and 2S-E8-E10-13 OAc (10 1 1 1 ng) and 4Z,2S-E10-13 OAc, 2S-13 OAc, 2S-E10-13OH and 2S-Z8-E10-13 OAc (10 1 1 1 ng) A) blank-blank, chi$^2$=O 048, p>O 05, B) blank-7, chi$^2$=33 92, p<O 001, C) 1-3, chi$^2$=10 29, p<O 01, D) 1-4E, chi$^2$=5 59, p<O 05, E) 3-4E, chi$^2$=1 72, p>O 05, F) 3-4Z, chi$^2$=1 53, p>O 05, G) 4E-4Z, chi$^2$=2 77, p>O 05 and H) 4Z-extract, chi$^2$=17 47, p<O 001*=p<O 05, =p<O 01 and *=p<O 001
Figure 8:
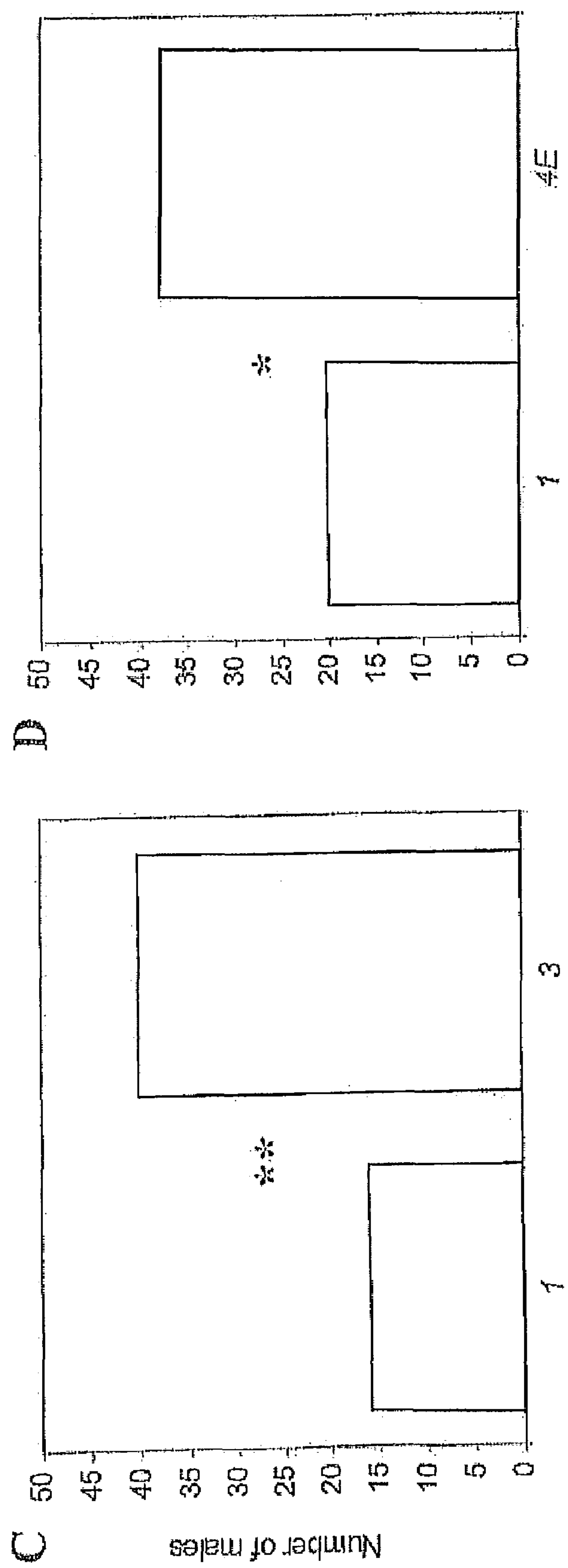
Figure 8:
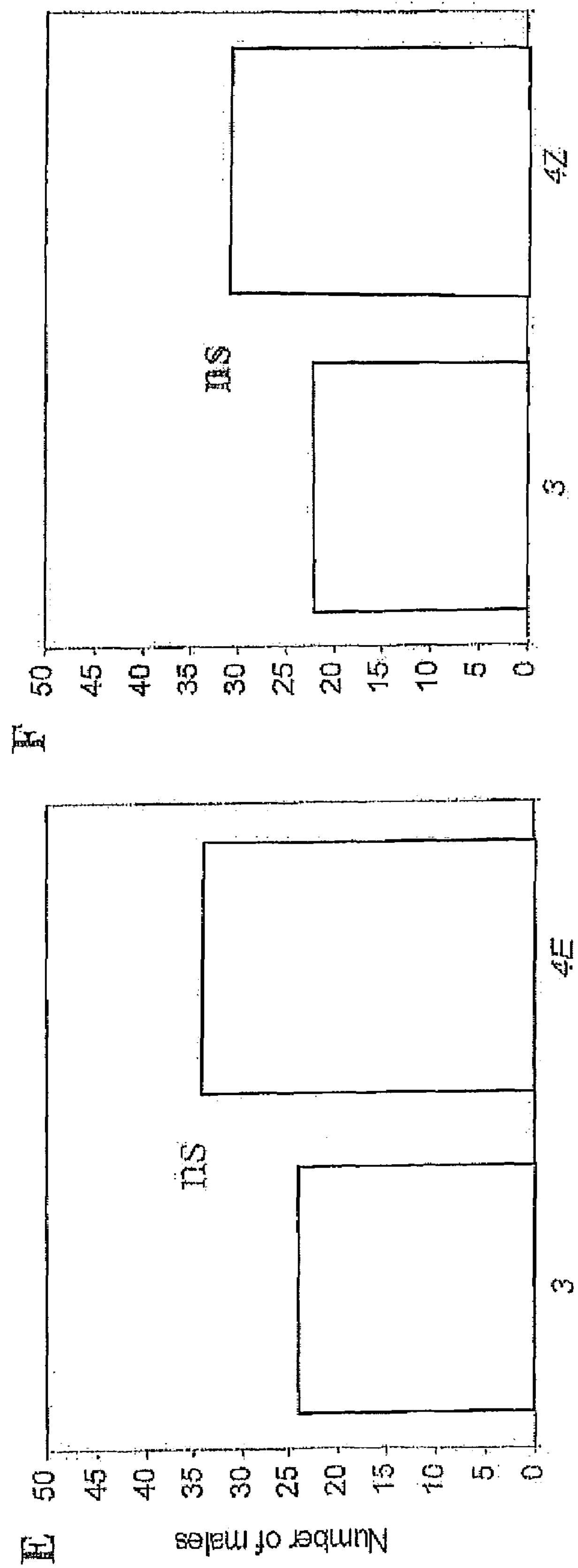
Figure 8:
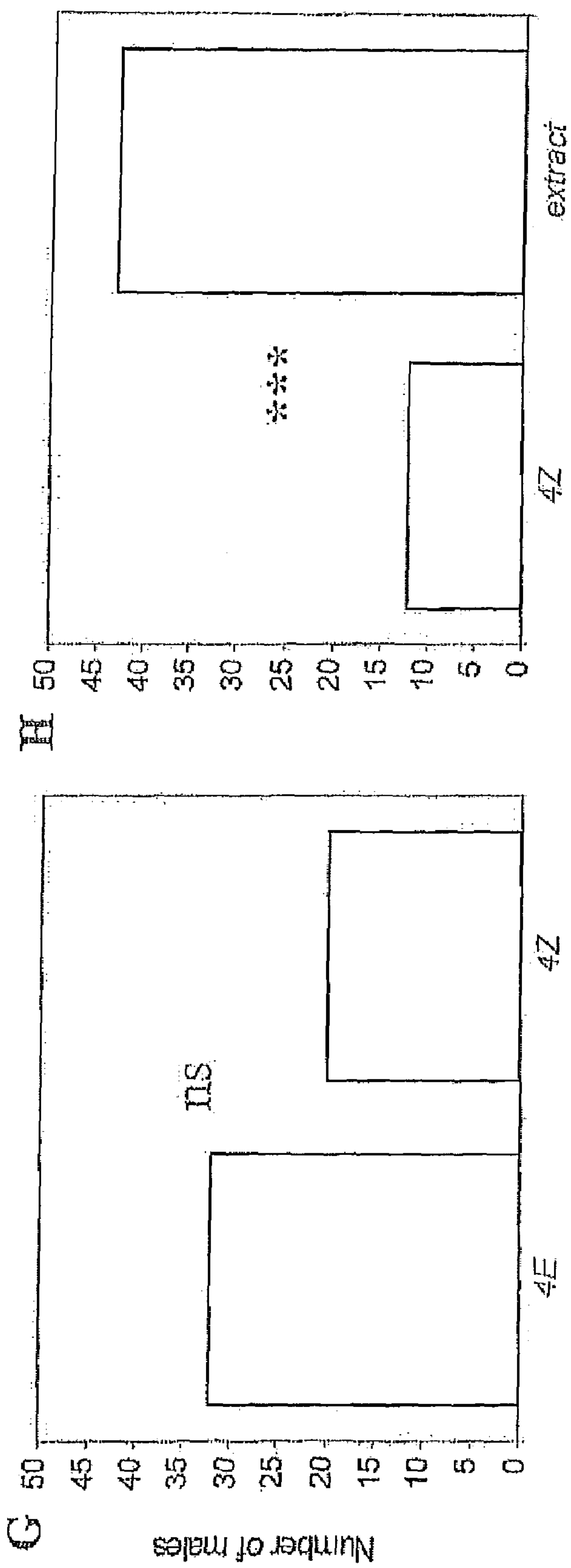

| Bioassay | N | Number of responding males | Responding males (%) | FIG. 8 |
|---|---|---|---|---|
| blank—blank | 40 | 21 | 53 | A |
| blank-1 | 60 | 52 | 87 | B |
| 1-3 | 60 | 56 | 93 | C |
| 1-4E | 60 | 58 | 97 | D |
| 3-4E | 60 | 58 | 97 | E |
| 3-4Z | 60 | 53 | 88 | F |
| 4E-4Z | 60 | 52 | 87 | G |
| 4Z-extract | 60 | 55 | 92 | H |

Males did not have non-odour mediated directional preferences as shown by the blank-blank bioassay ($chi^2$=0 048, p>0 05) (FIG. 8A) When blank was tested against the main pheromone compound (1), males were significantly more attracted to the latter ($chi^2$=33 92, p<O 001) (FIG. 8B) However, both 3 and 4E were significantly more attractive than 7 in the 1-3 ($chi^2$=10 29, p<O 01) and 1-4E bioassays ($chi^2$=5 59, p<0 05) (FIGS. 8C-D) Due to these results, 4Z was not tested against 7 Both 4E and 4Z showed a tendency to be more attractive than 3, but the differences in the number of attracted males were not significant in the 3-4E ($chi^2$=1 72, p>0 05) and 3-4Z bioassays ($chi^2$=1 53, p>0 05) (FIGS. 8E-F) Moreover, when the two four-component blends were tested against each other, 4E attracted more males than 4Z, but the difference was not significant ($chi^2$=2 77, p>0 05) (FIG. 8G) Since the amount of female gland extract was limited, only one bioassay that included gland extract was conducted Due to the fact that 2S-Z8-E10-13 OAc had a retention time and mass spectrum that closely fitted the unidentified double-unsaturated $C_{13}$ acetate in female extracts, 4Z was tested against extract The result from this comparison showed that gland extract was significantly more attractive than 4Z ($chi^2$=17 47, p<0 001) (FIG. 8H)

The chemical structure of Hessian fly pheromone components is similar to other gall midges The pheromone components are chiral as are all other identified pheromone components in gall midges, and the male response is enantiomer-specific (Hillbur et al 2001, 2005) Moreover, all so far identified Hessian fly pheromone compounds have 13 carbon chains (although there are indications of an existing $C_{15}$ acetate) and all have a functional group in C-2 position This is also typical for gall midge pheromone components, although shorter and longer carbon chains exist However, the Hessian fly pheromone also differs from the identified pheromones of other gall midges GC-EAD analyses of female gland extract indicate that the pheromone contains seven components The orange wheat blossom midge, the aphidophagous gall midge and the Douglas-fir cone gall midge all have reported pheromones consisting of only one compound The pea midge (Hillbur eif at 1999), the swede midge (Hillbur at al 2005) and the red cedar cone midge have three components in their pheromones The pheromone components of the pea midge and the swede midge also show a strong synergism (Hillbur et al 2000, 2005) For these species, synthetic two-component blends were shown to be unattractive, while adding a third component made the pheromone blend as attractive as female extract, i e all three compounds were essential for attraction The same pattern of synergism has not been observed for the Hessian fly pheromone The results showed that the main component alone is able to attract males under laboratory conditions. The results from this study also showed that addition of two (or three) compounds increases the attractiveness of the stimulus. However, since all compounds in the pheromone are still not identified, it is possible that adding one of the unidentified compounds to the three- or four-component blends dramatically increases the attractiveness of the stimulus. The pheromone of the congeneric red cedar cone midge is also different from the Hessian fly pheromone. That pheromone of congeneric red cedar cone midge consists of three different (S,S)-diacetoxyheptadecanes, each being equally attractive as a blend containing all three. Such redundancy is not seen in the Hessian fly pheromone or in any other gall midge species.

The results of the behavioural part of this study are consistent with previous results. Hillbur at al (unpublished) showed, in a semi-field test, that males were less attracted to the main component alone than to the three-component blend. In agreement, my results showed that the three-component blend attracted significantly more males than the main component alone. This result confirmed the presence of 2S-13:OAc and 2S-E10-13:OH in the Hessian fly pheromone. In a wind tunnel study the main component attracted 56% of the males to the odour source. However, the main component alone did not catch any males in the field. In contrast, the results of the present study showed that the main component alone attracted over 90% of the responding males when it was compared to blank. This difference probably reflects the different methods used In a Y-tube, the distances are small and the insects only have three options. They can either: (i) not respond, i.e. no upwind orientation or (ii) choose one side-arm or (iii) choose the other arm, meaning that the behavioural repertoire is highly reduced. This differs from the wind tunnel where distances are much larger and the insects have more options. The difference is even more pronounced when tests are done in the field. Here, the synthetic lure has to compete with calling females over even longer distances. The decreased attractiveness of the main compound when it had to compete with more attractive stimuli was also shown in my experiments. Both 3 and 4E attracted significantly more males than 1 in the 1 vs. 3 and 7 vs. 4E bioassays.

Chemical analyses have indicated that an unsaturated $C_{15}$ acetate is present in Hessian fly gland extract and 2S-E10-15:OAc and 2S-E12-15:OAc have been proposed as candidate compounds. However, when analysed by GC-EAD, the two compounds did not elicit antennal responses in males, indicating that they are not included in the pheromone. Moreover, the retention times of these compounds did not fit with the retention times of the antennally active compounds in female extract. In order to reveal the identity of the active compound, unsaturated $Cl_5$ acetates with different double bond positions should be synthesized and tested on GC-EAD. Analyses of gland extract have also shown that a double-unsaturated $C_{13}$ acetate is present and elicits antennal responses. The GC-EAD results from this study showed that males respond to both 2S-E8-E10-13:OAc and 2S-Z8-E10-13:OAc. The mass spectrum and retention time of the Z,E isomer corresponded to the double-unsaturated $C_{13}$ acetate in gland extract (number 6 in FIG. 7). This indicated that the $Z_1E$ isomer was more likely to represent the double-unsaturated $C_{13}$ acetate than the $E_1E$ isomer. However, this was not confirmed in the behavioural tests, where the attractiveness of the 4Z blend did not differ from the 3 and 4E blends. Furthermore, 4E seemed to be the most attractive synthetic blend. These results indicate that none of the two isomers are inhibitory, at least not at the ratios tested, and that it is possible that both 2S-E8-E10-13:OAc and 2S-Z8-E10-13:OAc are pheromone components. The retention time of the $E_1E$ isomer corresponds with the compound in gland extract thought to be an unsaturated $C_{15}$ acetate (response number 7 in FIG. 7). The GC-EAD analyses of extract show a strong response to compound number 7 although it is present in undetectable amounts. If 2S-Z8-E10-13:OAc is a pheromone component, it is possible that response number 7 is to trace amounts of 2S-E8-E10-13:OAc. If this is the case, then the unsaturated $C_{15}$ acetate present in gland extract might be a pheromone component precursor. All pheromone components except one (number 1 in FIG. 7) would thus be identified. However, further studies are needed to evaluate this possibility.

The results from this study clearly show that the complete Hessian fly sex pheromone is still not identified since the 4Z blend was significantly less attractive than female gland extract. This result might have a number of explanations. The 4Z blend did not attract significantly more males than 3 or 4E and it can thus not be concluded that 2S-Z8-E10-13:OAc is a pheromone component. There are also additional antennal responses to unidentified compounds in gland extracts (FIG. 7). Probably, these compounds are necessary to obtain the full attractiveness of the pheromone. In addition, the exact ratio between the pheromone components might also be essential for maximum attractiveness (Linn & Roelofs 1995). The pheromone specificity for some species also depends on the geometric isomeric composition of pheromone compounds, and closely related species often use different isomers of the same compounds in their pheromone (Witzgall et al 1996). In these cases, the isomers that are not included in one species' pheromone often act as repellents and inhibit mate attraction. For instance, the main pheromone component of the pea moth (*Cydia nigricana*) is (8£,10E)-8,10-dodecadien-1-yl acetate and it has been shown that the E,Z, $Z_1E$ and the Z,Z isomers of the compound inhibit male attraction to the female sex pheromone (Witzgall et al 1993). Also, studies on the codling moth (*C. pomonella*) have shown that geometric isomers of the main pheromone component act inhibitory on male attraction (El-Sayed et a/1998).

Hessian fly male antennae respond to 2S-Z10-13:OAc in gland extracts. Due to 98% isomeric purity of synthetic compounds, a small amount of this compound was also present in the synthetic blends. If 2S-Z10-13:OAc acts as an attractant, the correct EfZ ratio of the main compound might be important to achieve proper attraction. Although, the results from Harris and Foster (1991) did not indicate that different EfZ ratios of the main compound affect male attraction, it might have an effect when more complex blends are used as stimuli, and also when the synthetic stimuli compete with female extract. The EfZ ratio in the synthetic blends probably deviated from the ratio in gland extract and could, at least in part, be responsible for the results observed. In addition, since the possibility also exist that both 2S-Z8-E10-13:OAc and 2S-E8-E10-13:OAc are pheromone compounds, it might be important to have the correct ratio of these isomers to achieve maximum attractiveness of the stimulus blend.

The only gall midge, except for the Hessian fly, that has been shown to utilize an unsaturated pheromone compound is the Douglas-fir cone gall midge. The pheromone of this species consists of the single compound (2S,4Z,7Z)-4,7-tridecadien-2-yl acetate. However, it has not been tested if the other geometric isomers have inhibitory effects on male attraction to the pheromone. To date, no results have shown that geometric isomers of Hessian fly pheromone compounds are inhibitory to male attraction. However, the presence of 2S-Z8-E10-13:OAc and perhaps also 2S-E8-E10-13:OAc in the pheromone must be confirmed or rejected. If it turns out that one or both compounds are pheromone compounds, the effect of the other two isomers (E, Z and $Z_1Z$) should be tested.

Thus in a further field trial a five-compound blend was tested as to dose-response, whereby the blends were absorbed on different absorbents in the form of cotton-wool pads, and polyethylene dispensing surfaces.

Thus in this further test the five components (2S,1 OE)-I O-tridecen-2-yl acetate (2S-E10-13:OAc), (2S)-tridecan-2-yl acetate (2S-13:OAc), (2S,10E)-10-tridecen-2-ol (2S-E10-13:OH), (2S,8£,10£)-8,10-tridecadien-2-yl acetate (2S-E8-E10-13:OAc) and (2S,8Z,10£)-8,10-tridecadien-2-yl acetate (2S-Z8-E10-13:OAc), were tested in amounts of 1 μg, 10 μg, and 100 μg, respectively, whereby the compositions were administered from a cotton-wool pad, and a polyethylene surface, respectively, comprising these amounts. The different components were present in the ratios 10 (2S-E10-13:OAc):1(2S-13:OAc):1(2S-E10-13:OH):1(2S-E8-E10-13:OAc):1(2S-Z8-E10-13:OAc).

Over a 9 days period the different amounts provided by the polyethylene surfaces attracted 7 (0.7%), 93 (9.8%), and 848 (89.5%), male Hessian flies, respectively. Thus it is apparent that there is a dose response when it comes to attraction of the Hessian fly. The cotton-wool pads provided little attraction, in comparison with the polyethylene surface.

Conclusions and future directions The results from this study confirmed that in addition to the main pheromone component (2S-E10-13:OAc), 2S-13:OAc and 2S-E10-13:OH are also included in the Hessian fly pheromone. It can also be concluded that the complete pheromone is still not identified. Furthermore, the presence of 2S-Z8-E10-13:OAc and 2S-E8-E10-13:OAc in the pheromone is still unclear.

The invention claimed is:

1. A pheromone composition for attracting male Hessian fly, *Mayetiola destructor* (Say), for monitoring and/or combating purpose, said composition consisting of (2S)-tridecan-2-yl acetate (2S-13:OAc), (2S,10E)-10-tridecen-2-yl acetate (2S-E10-13:OAc), [(2S,10E)-10-tridecen-2-ol (25-E10-13:OH), (2S,8E,10E)-8,10-tridecadien-2-yl acetate (2S-E8-E10-13:OAc) and (2S,8Z,10E)-8,10-tridecadien-2-yl acetate (2S-Z8-E10-13:OAc).

2. A pheromone composition according to claim 1, wherein the ratio between (2S-E10-13:OAc), (2S-13:OAc), and (2S-E10-13:OH) is 10:1:1.

3. A pheromone composition according to claim 1, wherein the ratio between (2S-E10-13:OAc), (2S-13:OAc), (2S-E10-13:OH) and (2S-E8-E10-13:OAc) is 10:1:1:1.

4. A pheromone composition according to claim 1, wherein the ratio between (2S-E10-13:OAc), (25-13:OAc), (2S-E10-13:OH), (2S-E8-E10-13:OAc) and (2S-Z8-E10-13:OAc) is substantially 10:1:1:1:1.

5. A method for attracting male Hessian fly, *Mayetiola destructor* (Say), comprising dispersing in an environment comprising said Hessian fly a composition consisting of (2S,10E)-10-tridecen-2-yl acetate (2S-E10-13:OAc), (2S)-tridecan-2-yl acetate (2S-13:OAc), (2S, 10E)-10-tridecen-2-ol (2S-E10-13:OH), (2S,8E,10E)-8,10-tridecadien-2-yl acetate (2S-E8-E10-13:OAc) and (2S,8Z,10E)-8,10-tridecadien-2-yl acetate (2S-Z8-E10-13:OAc) in an amount which is effective to attract said Hessian fly.

* * * * *